(12) United States Patent
Gillard et al.

(10) Patent No.: US 8,961,519 B2
(45) Date of Patent: Feb. 24, 2015

(54) SURGICAL ROTARY CUTTING TOOL AND TOOL GUARD ASSEMBLY

(75) Inventors: Duane Lee Gillard, Pierceton, IN (US);
Eric Manojlovic, Fort Wayne, IN (US);
Jenna Ross, Columbia City, IN (US);
Jerry Lower, Bourbon, IN (US)

(73) Assignee: Zimmer, Inc., Warsaw, IN (US)

( * ) Notice: Subject to any disclaimer, the term of this patent is extended or adjusted under 35 U.S.C. 154(b) by 581 days.

(21) Appl. No.: 12/950,323

(22) Filed: Nov. 19, 2010

(65) Prior Publication Data

US 2012/0130375 A1 May 24, 2012

(51) Int. Cl.
*A61B 17/16* (2006.01)

(52) U.S. Cl.
CPC ......... *A61B 17/1633* (2013.01); *A61B 17/1617* (2013.01)
USPC .......................................... 606/80

(58) Field of Classification Search
USPC ........... 606/79, 80, 87, 96; 408/127; 384/129, 384/142, 290
See application file for complete search history.

(56) References Cited

U.S. PATENT DOCUMENTS

| | | | | |
|---|---|---|---|---|
| 2,878,809 A | * | 3/1959 | Treace | 606/170 |
| 3,945,375 A | * | 3/1976 | Banko | 600/104 |
| 4,944,642 A | * | 7/1990 | Andersson | 408/241 R |
| 5,782,844 A | * | 7/1998 | Yoon et al. | 606/139 |
| 6,443,966 B1 | * | 9/2002 | Shiu | 606/159 |
| 7,625,409 B2 | | 12/2009 | Saltzman et al. | |
| 7,780,673 B2 | | 8/2010 | Acker et al. | |
| 7,780,691 B2 | | 8/2010 | Stefanchik | |
| 2003/0130663 A1 | * | 7/2003 | Walen | 606/80 |
| 2006/0241629 A1 | | 10/2006 | Krebs et al. | |

OTHER PUBLICATIONS

Product Catalog—vol. 8, Brasseler USA Surgical Power & Accessories, 2005 Brasseler USA Medical, LLC.
Product Brochure, Hall MicroPower, ConMed Linvatec, 2007 Linvatec Corporation, a subsidiary of ConMed Corporation Jan. 2007.
Product Brochure, Ultrapower, ConMed Linvatec, 2011, 2010 Linvatec Corporation, a subsidiary of ConMed Corporation Mar. 2011.
Product Brochure—Miniature & Instrument Bearings for Medical and Dental Applications, National Precision Bearing—dated May 21, 2008.
Part Numbering System, National Precision Bearing, accessed at http://www.nationalprecision.com/miniature-bearings/part_numbering_system.html—accessed on Oct. 1, 2010, Copyright 2010.

* cited by examiner

*Primary Examiner* — Christian Sevilla
(74) *Attorney, Agent, or Firm* — Schwegman Lundberg & Woessner, P.A.

(57) ABSTRACT

A surgical rotary cutting tool and guard assembly is provided in which the cutting tool has a shaft with a proximal end and a distal end with an end effector at the distal end. The shaft includes at least one bearing mounted thereto intermediate the proximal and distal ends, the bearing having an inside dimension and the shaft having an outside dimension that provide for an interference fit between the bearing and the shaft. A tubular sleeve that serves as a guard houses the shaft, the sleeve having an inside dimension sized to slidably support the bearing.

20 Claims, 3 Drawing Sheets

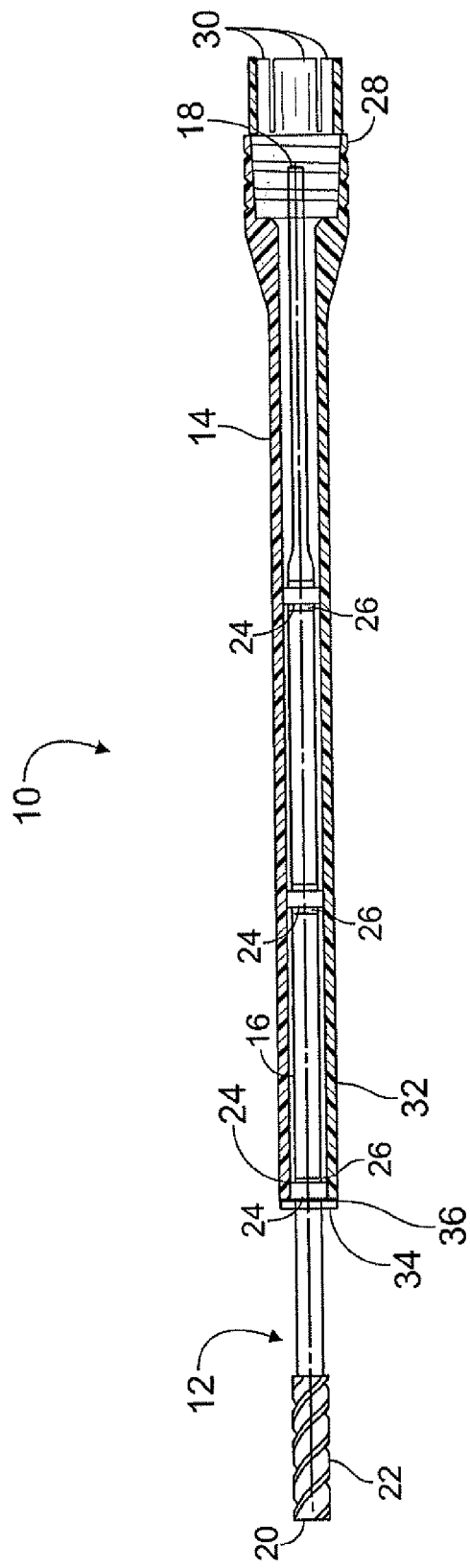

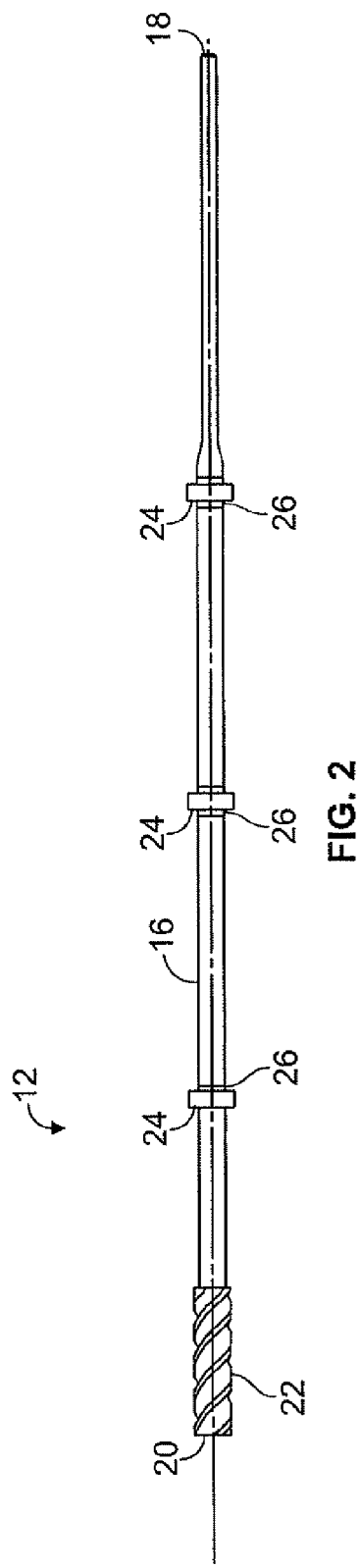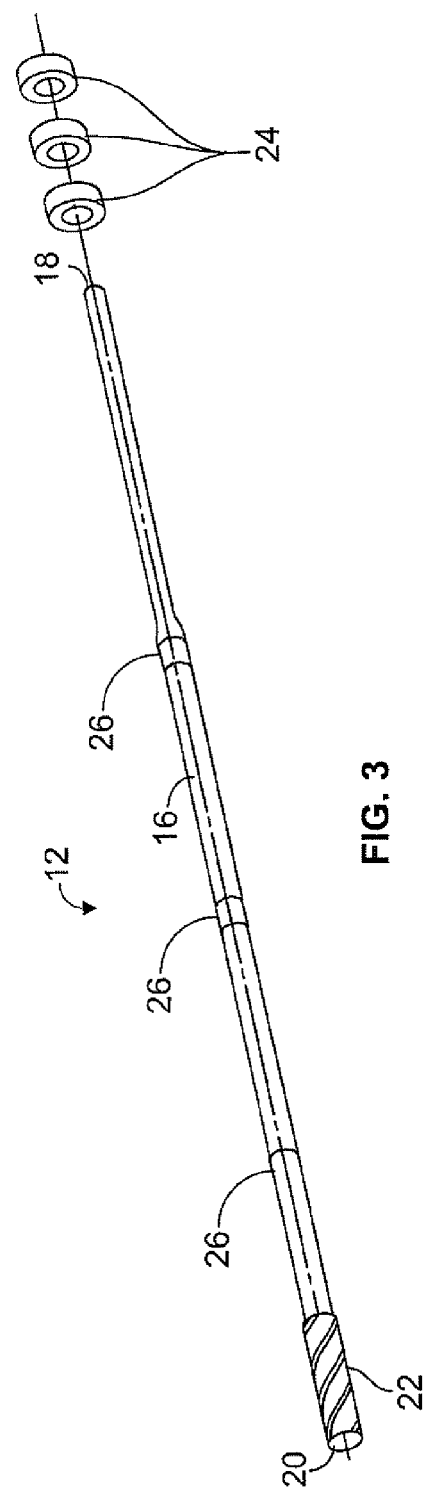

SURGICAL ROTARY CUTTING TOOL AND TOOL GUARD ASSEMBLY

FIELD OF THE DISCLOSURE

The present disclosure relates to a surgical rotary cutting tool and tool guard assembly, and more particularly, but not exclusively, to a surgical burr and burr guard assembly. The tool and guard assembly may be suited for use, for example, in joint replacement and similar surgical procedures in which the burr is intended for a single use, while the burr guard is intended for multiple uses.

BACKGROUND

In performing joint replacement surgeries, such as for hips, knees and ankles, bone often must be removed and/or resurfaced to better accept the prosthesis. The bone removal/resurfacing is typically done with a drill-like device having a cutting surface or burr having a shaft that is secured to and rotated by a motorized hand piece. The burr may be used with a sleeve or guard which houses the shaft and provides a support surface which may be gripped by the surgeon or secured to a jig.

To the extent that surgical devices and instruments are used for more than a single surgical procedure, the ability to easily and effectively sterilize the device is of concern. In order to be effectively sterilized, instruments must first be thoroughly cleaned. Otherwise, the debris that remains on the surface of the instrument may form a protective barrier that shields microbes from destruction when sterilized. Because of these difficulties, many surgical instruments are used once, and then disposed of, rather than risk a second use of an instrument that has not been effectively sterilized. Notwithstanding the benefits of disposability, the materials and manufacturing costs associated with some surgical instruments are sufficiently high that to limit the instrument to a single use before disposal is unduly expensive. Consequently, some instruments are designed to have both disposable and reusable components. A continuing challenge when designing surgical instruments that comprise both single use and reusable components is to configure the device so that the disposable components are relatively inexpensive while the reusable components can be easily and effectively cleaned and sterilized. In the context of the present disclosure, there is a continuing need to address such challenges and to provide surgical rotary cutting tool and guard assemblies that reduce the cost without presenting undue sterilization challenges.

SUMMARY

In a first aspect, the present disclosure relates to a surgical rotary cutting tool comprising a shaft with a rotary end effector at its distal end. The shaft has at least one bearing mounted thereon intermediate the proximal and distal ends, with the bearing having an inside dimension and the shaft having an outside dimension that provide for an interference fit between the bearing and the shaft.

In another aspect of the disclosure, the shaft has a second outside dimension that is smaller than the first outside dimension so as to define a land on the shaft where the bearing is intended to be located.

In a further aspect of the disclosure, the cutting tool is used in combination with a tubular sleeve or guard. The sleeve includes a bore having an inside dimension sized to slidably support the bearing on the shaft of the cutting tool.

In another aspect of the disclosure, the sleeve may comprise an internal stop that defines an inside dimension that is sized smaller than the outside dimension of the bearing. The stop limits the distal extent to which the burr can extend beyond the distal end of the sleeve. Specifically, the bearing cannot move distally within the sleeve beyond the stop, thus limiting the distal travel of the burr. Preferably, the stop is on the distal end of the sleeve and comprises an insert received therein that creates the stop.

In another aspect of the disclosure, the assembly of a surgical cutting tool and guard is provided in which the cutting tool and the guard have one or more of the features set forth above, in any combination.

In another aspect of the disclosure, a method is provided for making a rotary cutting tool having a shaft with at least one bearing mounted thereon.

BRIEF DESCRIPTION OF THE DRAWINGS

In the course of this description, reference will be made to the accompanying drawings, wherein:

FIG. 1 is a plan view in partial cross section showing the combination of a rotary surgical cutting tool and guard in an exemplary embodiment of a burr and burr guard in accordance with the present disclosure, with the burr in the extended, working position.

FIG. 2 is an enlarged plan view of the surgical burr in accordance with the present disclosure;

FIG. 3 is an exploded perspective view of the surgical burr of FIG. 2;

DETAILED DESCRIPTION

Figure 4:
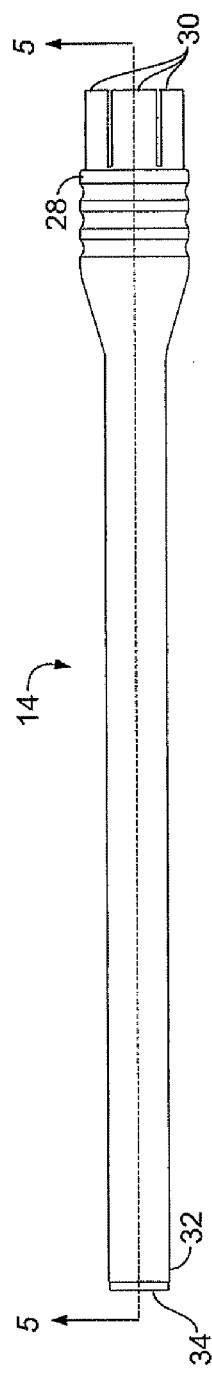
FIG. 4 is a plan view of the burr guard or sleeve in accordance with the present disclosure that may be used in combination with the surgical burr of FIGS. 2 and 3.
Figure 5:
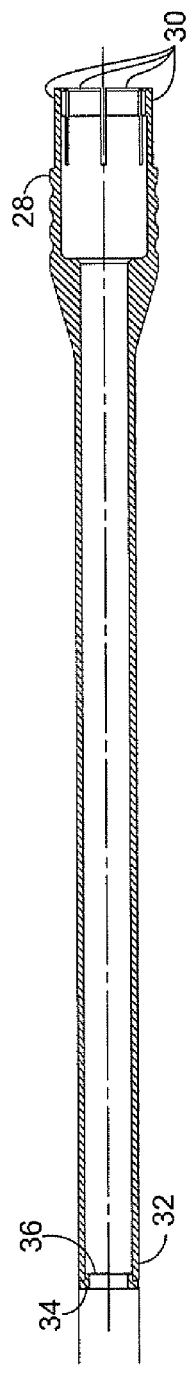
FIG. 5 is a cross sectional view of the burr guard of FIG. 4.
Figure 6:
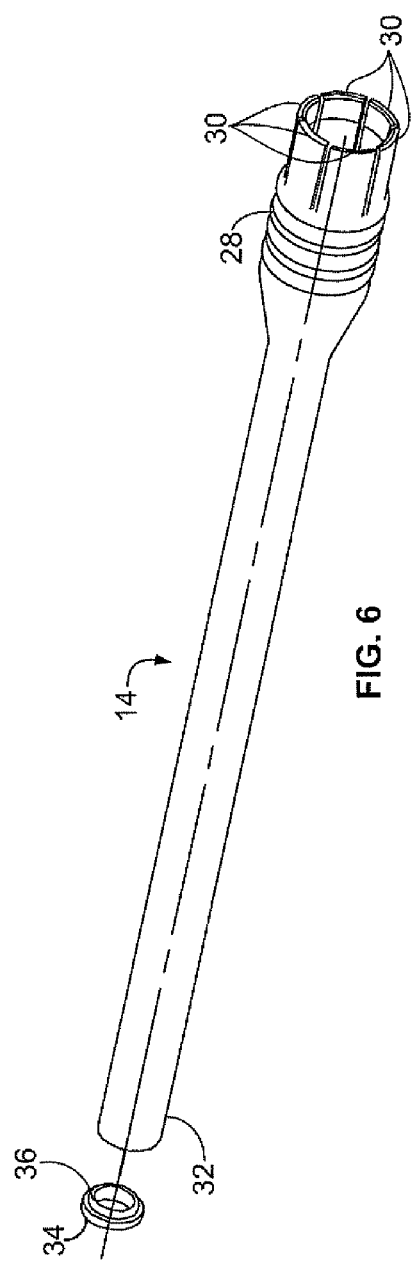
FIG. 6 is an exploded view of the burr guard of FIG. 4.

The detailed embodiments disclosed herein are exemplary and for the purposes of describing and illustrating the subject matter of the disclosure, which may be embodied in various alternative forms. Therefore, specific details disclosed herein are not to be interpreted as limiting, but as exemplary and explanatory for informing those skilled in the art of the subject matter.

As noted above, the present disclosure relates to a rotary cutting tool and guard assembly for surgical use and, by way of example and not limitation, to a surgical burr and burr guard assembly suited for use in joint replacement surgical procedures. In accordance with an aspect of this disclosure, the cutting tool (i.e., the shaft, end effector and bearings) is suitable for a single use and for disposal thereafter. This eliminates the need for the user to attempt to clean and sterilize the intricate surfaces and structures of the bearings and end effector, as these structures present a particular challenge for many methods of sterilization. Locating these structures on the shaft permits convenient disposal, if desired.

Turning to FIG. 1, there is seen one embodiment, generally designated 10, of the combination of a disposable surgical burr 12 and a sterilizable and reusable burr guard 14 in accordance with the present disclosure. The burr 12 comprises a shaft 16, which is preferably, but not necessarily, unitary or comprises a single piece. The shaft 16 has a proximal end 18 that is sized and shaped in length and diameter so as to be receivable into the rotatable chuck of a motorized hand piece (not shown). Suitable hand pieces may be obtained from Brasseler USA of Savannah, Ga. or Conmed Linvatec of Largo, Fla. As illustrated, the proximal end 18 is reduced in diameter relative to the remainder of the shaft, although this is not required.

The shaft 14 further comprises a distal end 20 on which is an end effector 22. The end effector 22 has a cutting surface and is intended to be rotated for removing and/or resurfacing bone. As illustrated, the end effector 22 is in the form of a burr having spiral flutes. However, the end effector 22 may have other configurations appropriate for surgical rotary cutting tools, such as rounded or spherical, acorn-shaped, oval, tapered, etc. The shaft 16 preferably has a unitary or one-piece configuration, and suitable materials for the shaft include stainless steel or other materials having sufficient strength and rigidity.

In keeping with one aspect of the disclosure, the shaft 16 has one or more bearings 24 seated thereon. As shown, three bearings 24 are mounted to the shaft 16 that are equidistantly spaced along the length of the shaft 16. The bearings 24 are mounted on the shaft 16 so that the inner race rotates with the shaft 16 while the remainder of the bearing 24 spins freely. Greater or fewer bearings 24 may be used and their spacing along the shaft 16 varied, depending on the length and flexibility of the shaft 16, in order to control the vibration of the shaft 16 when in use. Suitable bearings may be obtained from National Precision Bearing Group of Preston, Wash., which makes a range of miniature and instrument stainless steel bearings for medical and dental applications.

In keeping with a further aspect of the disclosure, the bearings 24 are preferably maintained in position on the shaft 16 by an interference or friction fit between the surfaces defining the inside dimension (e.g., diameter) of the inner race of the bearing and the outside dimension (e.g., diameter) of the shaft. Specifically, the inside dimension of the inner bearings race and the outside dimension of the shaft are nominally the same (e.g., with an interference of 0.0002 inches), allowing the bearing 24 to be press-fit onto the shaft 16 at the desired location.

As used herein, the terms "inside dimension" and "outside dimension" are used in describing certain aspects of the burr and the burr guard. The use of such terms is not intended to indicate that these components are required to have any particular cross sectional shape, but is more broadly intended to refer to the cross-sectional size and shape of the component, without regard to any particular shape. With reference to the following description, the outside dimensions and inside dimensions of mating components are to have complementary sizes and shapes. They may have circular cross-sections, and while this is the case for the illustrated embodiment, it is not required.

The bearings 24 are assembled onto the shaft 16 by sliding the bearings 24 along the shaft 16 until the desired position is reached. In the illustrated burr 12, the end effector 22 has a larger diameter than the remainder of the shaft 16. Thus, as shown in FIG. 3, the bearings 24 are mounted onto the shaft 16 by placing them over the proximal end 18 of the shaft 16 and then sliding them into position. In an exemplary embodiment, at least one of the two opposed surfaces of the bearings 24 is not shielded, and no lubricant is used in the bearing 24, in order to facilitate cleaning and sterilization of the burr 12 prior to use.

In accordance with another aspect of the disclosure, assembly of the bearings 24 onto the shaft 16 is facilitated by reducing the diameter of the shaft 16 between the lands 26 where the bearings 24 are to be seated. Thus, the bearings 24 may slide freely along the shaft 16 distally to the land 26, and then press fit into place or advanced over the land 26 to the next distal land 26 until the desired location is reached. When assembling the bearings 24 onto the shaft 16, the friction fit between the bearings 24 and the lands 26 needs to be overcome in order to move the bearings 24 distally along the shaft 16.

In one example, the outside dimension of the shaft 16 between the lands 26 is from between approximately 0.0015 to 0.0035 inches less than the outside dimension of the shaft 16 in the area of the lands 26 and is preferably about 0.0025 inches less. As can be appreciated, the outside dimension of the shaft 16 does not need to be reduced distally of the land 26 for the distal-most bearing 24.

As noted above, the shaft 16 is axially slidably and removably received within a cutting tool guard, such as the illustrated burr guard or sleeve 14. The burr guard or sleeve 14 is adapted for fixed and stationary mounting to the hand piece. To this end, the burr guard 14 has an enlarged proximal end 28 of a standard configuration so as to be useable with the various commercially-available hand pieces. As illustrated, the proximal end 28 includes slots that define arcuate fingers 30 that assist in orienting and securing the burr guard 14 relative to the hand piece. Suitable materials for the burr guard 14 include stainless steel, although other materials having sufficient strength, durability, and ability to withstand repeated sterilization may be used.

The burr guard 14 has an internal bore that extends fully between the proximal end 28 and distal end 32 of the guard 14. The bore has a substantially uniform inside dimension, with the inside dimension of the bore being sized and shaped so as to permit the bearings 24 to freely slide as the burr 12 is moved axially within the burr guard 14. In one example, the inside diameter of the burr guard 14 is approximately 0.002 to 0.0027 inches larger than the outside diameter of the outer race of the bearings 24. Because the interior of the burr guard 14 is generally smooth and straight, it is more easily cleaned between uses and is more likely to be effectively sterilized than the cutting tool.

In keeping with another aspect of the disclosure, the burr guard 14 is provided with a stop that limits the distal axial movement of the burr 12 relative to the burr guard 14. The stop may comprise a shoulder formed on the interior of the burr guard 14 that will be abutted by a bearing 24 as the burr 12 is moved distally within the burr guard 14. This allows rotation of the cutting tool, while preventing further axial movement or unintended axial migration of the cutting surface.

In the illustrated embodiment, the stop is created by a separate insert or plug 34 received in the distal end of the burr guard 14. The insert 34 provides an annular opening and forms a shoulder 36 having an inside dimension smaller than the outside dimension of the bearings 24, but larger than the outside dimension of the end effector 22. Thus, the shoulder 36 limits the extent to which the burr 12 could possibly move distally relative to the burr guard 14. Alternatively, the stop may be formed integrally with the burr guard 14.

The insert 34 may be made separately from the remainder of the burr guard 14 and may be secured thereto by any suitable means, such as by welding, a press fit, adhesive, or the like. Suitable materials for the insert 34 include stainless steel. While the stop in the illustrated burr guard 14 is located on the distal end 32 of the burr guard 14, it could be located at a portion of the interior of the burr guard 14 intermediate to proximal and distal ends as long as the end effector 22 is capable of being advanced a suitable distance beyond the distal end 32 of the burr guard 14 before the stop is engaged.

While the burr and burr guard assembly described above is illustrative of the principles of the present subject matter, numerous modifications may be made by those skilled in the art without departing from the spirit and scope of the following claims, including combinations of features that are individually disclosed or claimed herein. Accordingly, the scope hereof is not limited to the embodiments described above, but is as set forth in the following claims.

What is claimed is:

1. A surgical rotary cutting tool comprising:
a rigid shaft with a proximal end portion and a distal end portion with a rotary end effector, sufficiently hard to remove or resurface bone, at the distal end portion, the shaft having at least one bearing mounted to the shaft intermediate the proximal and distal end portions, the bearing having an inside dimension and the shaft having a first outside dimension that provide for an interference fit between the bearing and the shaft; and
a rigid, unitary tubular sleeve having a proximal end portion and a distal end portion, the sleeve having a bore extending between the proximal and distal end portions, the bore having an inside dimension sized to slidably support the bearing, such that the shaft and the bearing are moveable axially and rotationally within the sleeve.

2. The surgical cutting tool of claim 1 wherein the shaft of the cutting tool has a second outside dimension smaller than the first outside dimension such that the bearing moves freely along the shaft in the area of the second outside diameter.

3. The surgical cutting tool of claim 1 wherein the end effector of the shaft comprises a cutting surface.

4. The surgical cutting tool of claim 3 wherein the cutting surface comprises spiral flutes.

5. The surgical cutting tool of claim 1 wherein the sleeve comprises an internal stop, the stop defining an inside dimension sized smaller than an outside dimension of the bearing.

6. The surgical cutting tool of claim 5 wherein the stop is on the distal end portion of the sleeve.

7. The surgical cutting tool of claim 6 wherein the stop comprises an insert received in the distal end portion of the sleeve.

8. A surgical rotary cutting tool for use with a guard, the cutting tool being axially movable relative to the guard between a retracted position and a working position, the cutting tool comprising:
a rigid shaft with a proximal end portion and a distal end portion, with a rotary end effector, sufficiently hard to remove or resurface bone, at the distal end portion, the shaft having at least one bearing mounted thereto intermediate the proximal and distal end portions, the bearing having an inside dimension and the shaft having a first outside dimension that provide for an interference fit between the bearing and the shaft;
a rigid, unitary tubular sleeve having a proximal end portion and a distal end portion, the sleeve having a bore extending between the proximal and distal end portions, the bore having an inside dimension sized to slidably support the bearing, such that the shaft and the bearing are moveable axially and rotationally within the sleeve; and
the bearing being sized to be slidably supported within the guard such that the shaft is moveable longitudinally within the guard.

9. The cutting tool of claim 8 wherein the shaft of the cutting tool has a second outside dimension smaller than the first outside dimension such that the bearing moves freely along the shaft in an area of the second outside dimension.

10. The cutting tool of claim 8 wherein the end effector of the shaft comprises a cutting surface.

11. The cutting tool of claim 10 wherein the cutting surface of the end effector of the shaft comprises spiral flutes.

12. A surgical rotary cutting tool and guard assembly comprising:
a cutting tool that is sufficiently hard to remove or resurface bone and having a rigid shaft with a proximal end portion and a distal end portion, the shaft having at least one bearing mounted thereto intermediate the proximal and distal end portions, the bearing having an inside dimension and the shaft having a first outside dimension that provide for an interference fit between the bearing and the shaft; and
a rigid, unitary tubular sleeve having a proximal end portion, a distal end portion, and a bore extending between the proximal and distal end portions, the bore having an inside diameter sized to slidably support the bearing and having a stop formed thereon for limiting the distal movement of the shaft within the sleeve.

13. The assembly of claim 12, wherein the shaft of the cutting tool has a second outside dimension smaller than the first outside dimension such that the bearing moves freely along the shaft in an area of the second outside diameter.

14. The assembly of claim 12, wherein the shaft comprises a rotary end effector at the distal end portion thereof.

15. The assembly of claim 14, wherein the end effector of the shaft comprises a cutting surface.

16. The assembly of claim 15, wherein the cutting surface of the end effector comprises spiral flutes.

17. The assembly of claim 12, wherein the stop comprises an insert received in the distal end portion of the sleeve.

18. The assembly of claim 12, wherein the stop defines an inside dimension sized smaller than an outside dimension of the bearing.

19. The surgical cutting tool of claim 1, wherein the at least one bearing comprises an inner member and an outer member, wherein said inner member forms an interference fit with the shaft and said inner member rotates freely with the shaft.

20. The surgical cutting tool of claim 19, wherein said inner member comprises an inner race and said outer member comprises an outer race.

* * * * *